United States Patent
Nsofor

(10) Patent No.: US 7,067,163 B2
(45) Date of Patent: *Jun. 27, 2006

(54) SOY BASE AND RELATED METHOD OF MANUFACTURE

(75) Inventor: Leslie M. Nsofor, Lansing, MI (US)

(73) Assignee: Soy Ultima, L.L.C., East Lansing, MI (US)

( * ) Notice: Subject to any disclaimer, the term of this patent is extended or adjusted under 35 U.S.C. 154(b) by 326 days.

This patent is subject to a terminal disclaimer.

(21) Appl. No.: 10/169,321

(22) PCT Filed: Aug. 3, 2001

(86) PCT No.: PCT/US01/24267

§ 371 (c)(1),
(2), (4) Date: Jun. 26, 2002

(87) PCT Pub. No.: WO02/11557

PCT Pub. Date: Feb. 14, 2002

(65) Prior Publication Data

US 2003/0124223 A1    Jul. 3, 2003

Related U.S. Application Data

(63) Continuation-in-part of application No. 09/634,933, filed on Aug. 8, 2000, now Pat. No. 6,451,359.

(51) Int. Cl.
*A23J 3/16*     (2006.01)
*A23L 1/20*     (2006.01)

(52) U.S. Cl. .................. 426/46; 426/656; 426/634; 426/598

(58) Field of Classification Search ............... 426/46, 426/656, 634, 598
See application file for complete search history.

(56) References Cited

U.S. PATENT DOCUMENTS 4,041,187 A    8/1977    Nelson et al.
(Continued)

FOREIGN PATENT DOCUMENTS

EP    1120047    8/1999
(Continued)

OTHER PUBLICATIONS

Nsofor, L.M. et al. Storage stability and chemical properties of soymilk from sprouted soybeans. 1997; 34: 477-482, J. Fd. Sci. Technol.
(Continued)

*Primary Examiner*—Anthony Weier
(74) *Attorney, Agent, or Firm*—Warner Norcross & Judd LLP

(57) ABSTRACT

A process for producing a stabilized soy beverage from dehulled-whole soybeans partially hydrolyzed with enzymes. The process generally includes: providing whole soybeans (100); activating endogenous enzymes of the whole soybeans (110), hydrolyzing proteins in the soybeans (120); and hydrolyzing carbohydrates in the soybeans (130) to form a hydrolyzed soy base (140) including proteins and carbohydrates that do not form an observable colloidal phase. A preferred process includes: providing whole soybeans; hydrating the soybeans to activate endogenous enzymes within the soybeans; dehulling the soybeans; hydrolyzing the proteins within the dehulled soybean cotyledons by incubating the cotyledons at elevated temperatures; gelatinizing the incubated cotyledons to induce coagulation of the soybean polysaccharides; milling the gelatinized cotyledons into a slurry; hydrolyzing the polysaccharides of the cotyledons with the aid of added cellulose and/or hemicellulase to form a hydrolyzed soy base; deodorizing the slurry; mixing sweeteners, flavoring, and solubilization aids with the hydrolyzed soy base; homogenizing the hydrolyzed soy base; and heat treating the hydrolyzed soy base to form a soy beverage.

32 Claims, 2 Drawing Sheets

U.S. PATENT DOCUMENTS

| | | | |
|---|---|---|---|
| 5,989,600 A * | 11/1999 | Nielsen et al. | 426/52 |
| 6,024,990 A | 2/2000 | Kofoed et al. | |
| 6,322,846 B1 | 11/2001 | Gandhi et al. | |
| 6,410,064 B1 | 6/2002 | Akazawa | |
| 6,451,359 B1 * | 9/2002 | Nsofor | 426/46 |

FOREIGN PATENT DOCUMENTS

| | | |
|---|---|---|
| JP | 59135838 | 8/1984 |
| JP | 59203462 | 11/1984 |
| JP | 61192256 | 8/1986 |
| JP | 61219347 | 9/1986 |
| JP | 63169973 | 7/1988 |
| JP | 4053460 | 2/1992 |

OTHER PUBLICATIONS

Nsofor, L.M. & C.M. Osuji. Stability, rheology and chemical properties of soymilk concentrates developed from sprouted soybeans. 1997; 34:33-40, J. Fd. Sci. Technol.

Nsofor, L.M. & B.N. Azubike. Feasibility of shelf-stable soymilk from enzyme-hydrolyzed soybean flour. Oct. 1996. Paper presented at 5th Annual Conference of Nigerian Society for Biological Conservation.

Nsofor, L.M. Suitability of ultrafiltered soybean extract for developing evaporated cow milk analogue. 1996; 33:322-325, J. Fd. Sci. Technol.

Nsofor, L.M. Development of soybean-based milkshake analogue: final stage. 1995; Research report submitted to Federal University of Technology, Owerri, Nigeria.

Nsofor, L.M. & Ikegwuoha. Preliminary evaluation of polysaccharide hydrolysis during incubation of mashed sprouted soybeans. 1994; (Unpublished).

Nsofor, L.M. et al. Storage stability of concentrated soymilk; evaluation of cowmilk concentrate and salts' addition and soybean acid—steeping. 1993; 28:499-504, Inter. J. Fd. Sci. Technol.

Nsofor, L.M. Evaporated cow's milk analog development: stability of ultrafiltered extract of hydrolyzed soybeans. 1992; Research proposal submitted to International Foundation for Science, Stockholk, Sweden.

Nsofor, L.M. & Maduako. Stabilized soymilk for ambient tropical storage: a preliminary report. 1992; 27:573-576, Inter. J. Fd. Sci. Technol.

Nsofor, L.M. & K.B. Anyanwu. Development and evaluation of concentrated soy beverages. 1992(b) 29:331-332, J. Fd. Sci. Technol.

Nsofor, L.M. & K.B. Anyanwu. Effect of heat processing on refrigerated shelf-life of concentrated soymilk beverage. 1992(a); 29:40-44, J. Fd. Sci. Technol.

Smith, A.K.; Circle, S.J.; *Soybeans: Chemistry and Technology; The Avi Publishing Company, Westport,* Connecticut; pp. 358-359 (1972).

* cited by examiner

SOY BASE AND RELATED METHOD OF MANUFACTURE

This application is a continuation-in-part of U.S. application Ser. No. 09/634,933, filed Aug. 8, 2000 (now U.S. Pat. No. 6,451,359.

BACKGROUND OF THE INVENTION

The present invention relates to soy products, and more particularly to stabilized soy beverages manufactured from dehulled-whole soybeans.

Soybean or legume based food products are known for their high protein content and other health benefits such as the reduction of blood cholesterol and incidents of osteoporosis. The manufacture of soy beverage products presents a variety of distinct problems due to the chemical composition of the soybeans. For example, typical whole soy beverages usually have a chalky, gritty, or fibrous texture due to the complex carbohydrates present in the soybean cotyledons and hulls. Further, soy beverages are typically plagued with a "beany" flavor caused by enzyme activity, in particular, lipoxygenase activity, that results from the cell tissue of soybean cotyledons being disrupted in the presence of moisture and oxygen.

In conventional soy beverage manufacturing processes, these problems have been addressed. Typical soymilk beverages include a combination of water and soymilk concentrate produced from a process whereby whole soybeans are dehulled and blanched. To reduce the chalky texture of the soy beverage, the soybeans are dry-dehulled prior to processing. Dry-dehulling is the industrial process whereby the soybeans are heated so that the hull is separated from the cotyledon. The soybean hull is then physically cracked and subsequently separated from the cotyledon. Alternatively, the chalky texture may be reduced by extracting the soybeans. Conventional extraction includes crushing the whole soybeans in water and pressing the resultant slurry to squeeze out a soybean liquid. To address the "beany" flavor of the resultant soy beverage, the soybeans are blanched—that is, boiled or steamed at very high temperatures. Blanching inactivates the lipoxygenase enzyme present in the soybean and eliminates the possibility of the soybean developing the "beany" flavor during subsequent processing. During the blanching step, however, the soy proteins are substantially denatured whereby solubilization of the soy proteins is inhibited.

Although manufacture of prior art soy beverages removes the chalky texture and "beany" flavor of the beverage, a distinct problem arises during storage of the beverage in containers. In particular, the beverage is extremely unstable. The beverage separates into at least two layers; a clumpy colloidal (particle) phase at the base of the container, and a free whey water phase at the top of the container. Accordingly, the beverage becomes unattractive in this separated, clumpy-looking state. Further, consumers must vigorously shake the container to recombine the colloidal phase and water phase before consuming the beverage to avoid an unpleasant texture. In the prior art, it was thought that the denaturation of the protein during the application of heat to inactivate the lipoxygenase was the cause of the colloidal separation.

To eliminate the unattractive appearance of prior art soy beverages, manufacturers conventionally package the beverage in opaque containers such as laminated paper boxes or colored plastic bottles. Although this conceals the separation of the colloidal phase and the water phase, the soy beverage still must be shaken to uniformly distribute the soybean particles in the water phase and prevent clumping when the beverage is poured from the storage container.

Manufacturers of soy beverages of the prior art have also addressed soy beverage instability by isolating soy nutraceuticals, such as particular soy proteins and soy isoflavones from whole soybeans, and putting the nutraceuticals alone in a beverage. Although the resultant soy beverage is somewhat stable, only a select few soy nutraceuticals are present therein. Thus, consumers obtain a limited number of soy nutraceuticals when they consume these soy beverages rather than the synergistic composition of all the soybean's nutraceuticals.

SUMMARY OF THE INVENTION

The aforementioned problems are overcome in the present invention that provides a process for manufacturing a stabilized soy-base beverage from dehulled-whole soybeans that are hydrolyzed with enzymes. The soy base produced from the inventive process may be used to produce dairy/soy-based products, soy-based beverages and to nutritionally fortify a variety of foods. The resultant soy-based products exhibit stability for extended periods of storage, absence of a "beany" flavor and lack of a chalky texture. For example, during storage, the colloidal and water phases of a soy beverage created from the soy base do not separate, even for extended periods of storage. Before consuming the soy beverage, agitation of the soy beverage is unnecessary, as the colloidal and water phases do not separate in storage. Further, the soy beverage of the present invention is created from dehulled-whole soybeans; therefore all of the beneficial nutraceuticals of the dehulled-whole soybeans, such as soy proteins, isoflavones, trypsin inhibitors, saponins, phytates, phosphatides, fiber, omega-3-fatty acids and vitamin E, to name a few, are present in the resultant beverage.

It has been discovered that colloidal separation of conventional soy beverages during storage is caused by heat-induced binding and/or cross-linking of denatured proteins to carbohydrates in the soybean extract used to manufacture the beverage. After the proteins and carbohydrates bind together into large macro-molecules, the macro-molecules tend to clump together and separate and/or precipitate out from the liquid phase, thereby reducing the visual appeal of resultant soy beverages. According to this discovery, the process of the present invention enzymatically hydrolyzes the soy proteins and soy carbohydrates of whole soybeans into smaller molecules that are more soluble and thermodynamically stable in water after heat treatment. Thus, the resultant product of this process, a "hydrolyzed soy base," includes smaller molecules of carbohydrates and proteins, which are resistant to binding to one another and subsequent separation from a water or liquid phase.

The observed cross-linking of soybean carbohydrates with heat-denatured proteins in the soybean extracts after heating produces conjugates that are partially inert to human digestive enzymes and therefore depend on intestinal fermentation for hydrolysis of the soy carbohydrate/protein conjugates. Moreover, some individuals do not have the proper enzymes in their intestinal tract to ferment the conjugates and therefore find it difficult to digest soy beverages created with conventional processes. Because the hydrolyzed soybean base of the present invention includes a de minimis presence conjugates of protein and carbohydrates, most individuals can digest the base and absorb the soy nutrients without the discomfort of digestive fermentation.

In accordance with the above discoveries, the process of the present invention used to manufacture the hydrolyzed soybean base generally includes: providing whole soybeans that include carbohydrates and proteins; hydrolyzing the proteins; and hydrolyzing the carbohydrates so that the proteins and carbohydrates do not bind or cross-link to form colloidal masses or conjugates.

In a first embodiment of the present invention, the process of manufacturing a hydrolyzed soy base includes: providing whole soybeans; soaking and preliminarily incubating the whole soybeans so that endogenous enzymes of the soybean are brought to a potentially active state; dehulling the soaked soybeans and separating the wet hulls from the cotyledons; incubating the cotyledons at a temperature so that enzymes present in the soybean begin to hydrolyze the soy protein and carbohydrates; gelatinizing the partially hydrolyzed complex polysaccharides in the incubated cotyledons by high temperature treatment; milling the boiled cotyledons into a slurry; adding enzyme(s) to the slurry to further enhance hydrolysis of the soy carbohydrates therein and then subsequently deactivating the enzyme; and, deodorizing the cotyledon slurry to form a hydrolyzed soybean base.

In another embodiment, the soybeans used to make the hydrolyzed soy base in the preferred process are of high viability, that is, there is a relatively high probability that the soy proteins and/or carbohydrates will be hydrolyzed by endogenous enzymes in the soybean when the soybeans are rehydrated, preliminarily incubated and/or germinated. High viability soybeans are preferred over low viability because the high viability beans break down faster and do not ferment to cause a rancid flavor or odor during manufacture of the hydrolyzed soy base.

In yet another embodiment, the soybeans are steeped in a solution of citric acid, preferably before the soybeans are incubated to significantly reduce grittiness and/or chalkiness of resultant products created from the hydrolyzed soy base.

In a further embodiment, the enzyme added to assist hydrolyzing the soy carbohydrates is a cellulase/hemicellulase enzyme combination which enhances the hydrolysis of the soy carbohydrates.

In a further embodiment, the hydrolyzed soy base is multi-step homogenized, that is, soybeans are homogenized at an increasing pressure to provide a more homogenized soy base by sequentially breaking the soybeans into smaller and smaller particles. Preferably, the soybeans are gelatinized and/or milled before the multi-step homogenizing.

In a further embodiment, the process for formulating the hydrolyzed soybean base may be supplemented with additional steps to create a soy beverage. To formulate a soy beverage, the soy base may be modified in a process including: mixing sweeteners, stabilization aids, and coloring of the hydrolyzed soybean base; homogenizing the resultant formulated mix; and either sterilizing the homogenized formulation at ultrahigh temperatures for batches of the homogenized formulation to be stored at ambient temperature or pasteurizing the mix at lower temperatures for batches of the homogenized formulation to be refrigerated.

The hydrolyzed soy base manufactured from the process of the present invention has a wide variety of applications. For example, the soy base may be incorporated into—solely or in combination with—dairy or a variety of other food products such as beverages, yogurts, deserts, infant foods, cream liquors, puddings, creams, spreads, cheeses, mayonnaise, sherbets, tofu, yuba, aburrage, milkshakes and soups.

These and other objects, advantages, and features of the invention will be more readily understood and appreciated by reference to the detailed description of the preferred embodiment and the drawings.

DETAILED DESCRIPTION OF THE PREFERRED EMBODIMENT

I. General

Figure 1:
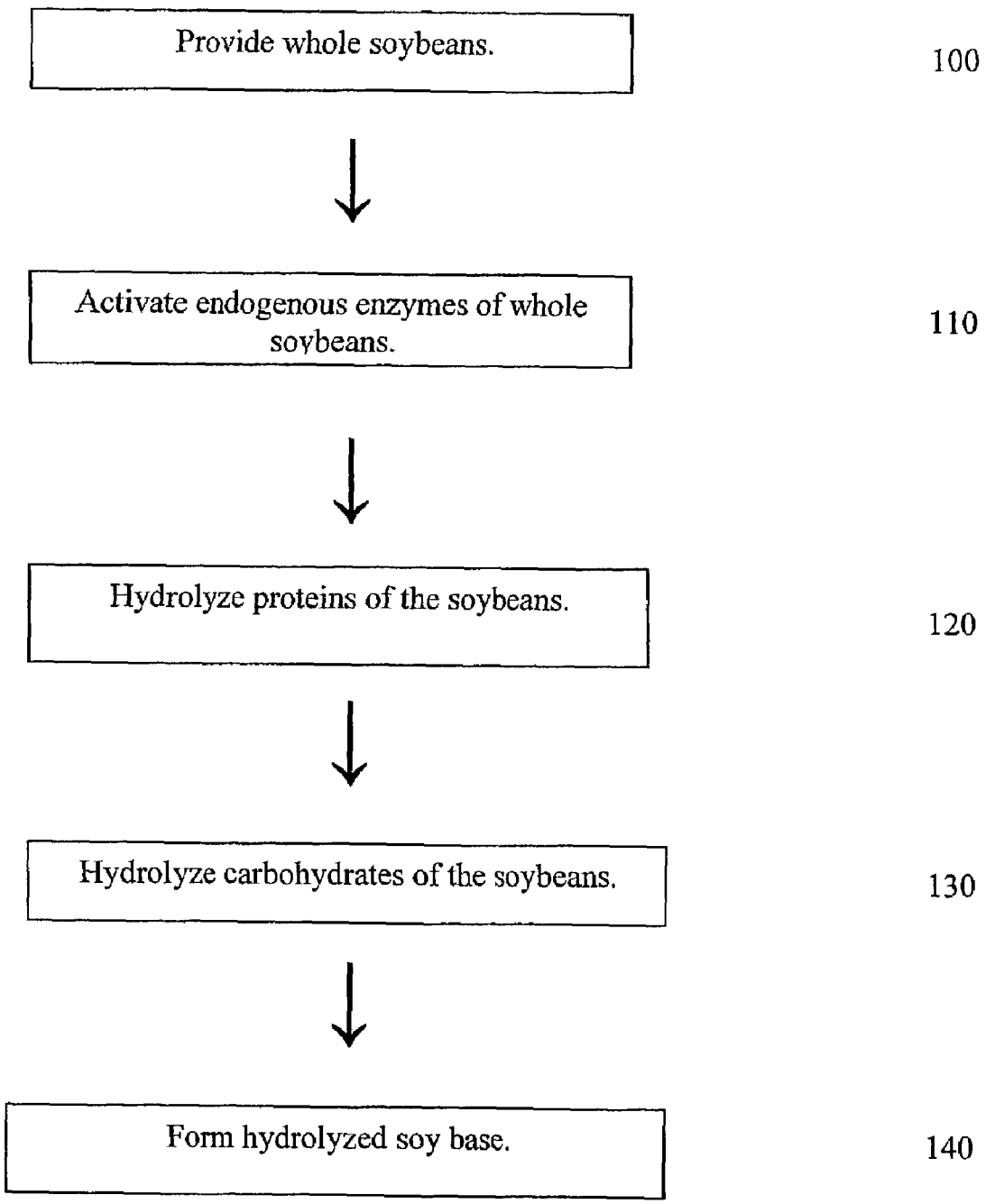
FIG. 1 shows a block diagram of the general process of the present invention used to manufacture a hydrolyzed soy base.

The present invention can be characterized as a method of manufacturing a soy base from hydrolyzed whole soybeans that may be combined with other ingredients to form a completed soy beverage. The soy base of this invention is an aqueous preparation of the soybean which exhibits: (a) stability of liquid soy base without separation of fat, sedimentation, or coagulation; (b) reduction of heat-induced or naturally occurring cross-linking of unhydrolyzed soy carbohydrates with denatured soy proteins; (c) prolonged storage life; (d) absence of soy flavor and associated "gritty" or "chalky" texture; (e) maximum blending capability with fruit juices, fruit juice blends and/or natural or artificial flavors; (f) enhanced compatibility with coloring agents; and (g) increased palatability.

The soymilk of the present invention preferably includes one or more of the following components, all of which are described in detail below: (a) a hydrolyzed soy base made from dehulled-whole soybeans; (b) water; (c) natural or artificial flavoring; (d) natural or artificial sweeteners; (e) stabilization aids; and (f) natural or artificial coloring.

II. Components

A. Hydrolyzed Soy Base From Whole Soybeans

The hydrolyzed soy base of the present invention is manufactured from whole soybeans. "Whole soybeans" are any known variety of soybeans with the hull intact. Whole soybeans include an exterior shell, or "hull" that encapsulates the inner portion of the soybean, or the "cotyledon." The "cotyledon" is the portion of the soybean used to produce the hydrolyzed soy base of the present invention. The cotyledon is comprised of a variety of different proteins including mono-, di-, and polypeptides, and sugars, including mono-, di-, and polysaccharides. The cotyledon also includes "endogenous enzymes," which are those enzymes that metabolize proteins and sugars of the cotyledon to promote germination and growth of the soybean plant. Other components and chemicals present in the cotyledon include isoflavones, goitrogens, phytestrogens, Bowman-Birk trypsin inhibitors, saponins, phytates, phosphatides, fiber, fatty acids, vitamins, and minerals.

As will be appreciated by those skilled in the art, the endogenous enzymes include proteinases that, when activated, hydrolyze proteins of the soybean and carbohydrases that, when activated, hydrolyze the carbohydrates of the cotyledons. Another endogenous enzyme present in soybean cotyledons responsible for hydrolysis of fatty acids is the enzyme lipoxygenase, which is also heat sensitive.

Preferably, the whole soybeans used to manufacture the hydrolyzed soy base are of an intermediate to high viability variety, that is, there is an intermediate to high probability that the soy protein and carbohydrates will be hydrolyzed by endogenous and/or added proteinases and carbohydrases as the soybeans are incubated, re-hydrated and/or germinated.

Generally, if desired, soybean viability may be categorized in any manner. In one embodiment, soybean variety may be divided into several gradations: low, intermediate and high. The degree of viability, when measured in percent germination during incubation, is the gross indicator of soybean endogenous enzyme activity. In the process of the present invention, incubation is the process by which soybeans are maintained in a state that is favorable to activate endogenous enzymes in the soybean so that the soybean begins to germinate and partially hydrolyze proteins and/or carbohydrates. Low viability soybeans exhibit less than 30% germination; intermediate viability soybeans exhibit about 30% to about 70% germination; and high viability soybeans exhibit greater than 70% to about 100% germination.

Preferred soybean cultivars may be selected from varieties including, but not limited to, Vinton 81, Ohio Vinton 81, and Wisconsin 2570 varieties, available from Thumb Oilseeds Producers Cooperative, Ubly, Mich., United States of America, and EC 1 and HP 204 varieties, available from Soyatech, Inc., Bar Harbor, Me., United States of America. As will be appreciated, the viability of the cultivars will change with storage conditions, seed drying conditions, and microbial/fungal infection of the cultivars.

It has been observed that high and intermediate viability soybeans exhibit many advantages over low viability varieties. For example, when low viability soybeans are used to make the hydrolyzed soy base in the processes below, several negative characteristics are observed, including reduced colloidal stability, rancid odor/taste attributes and gritty texture. As a result of reduced stability, more stabilizers and emulsifiers must be added which increases the viscosity of the resultant soy base. Moreover, in cases where low viability soybeans are used it is difficult to homogenize the resultant soy products because the unhydrolyzed soybean particles do not readily disintegrate in conventional homogenizers. As will be appreciated, however, low viability soybeans may be used in the process of the present invention as desired if the above negative attributes are acceptable for the application.

B. Water

Water contributes to the solubility and stabilization of the hydrolyzed soy base and the completed soy beverage. The water content in the hydrolyzed soy base in one embodiment is at least about 65 percent, in a second embodiment from about 65 percent to about 95 percent, in a third embodiment from about 80 percent to about 90 percent. Parts and percentages are by weight unless otherwise mentioned and temperatures are in degrees Celsius unless otherwise specified herein.

C. Additional Components

Sweeteners and stabilization aids may be added to the hydrolyzed soybean base to form a complete soy beverage.

"Sweeteners" include any chemical added to the soy beverage that enhances the sweet taste of the soy beverage. Exemplary sweeteners of a first embodiment of the invention are sucrose and fructose. Sucrose may be added in amounts from about 0% to about 10% in one embodiment, about 1% to about 6% in a second embodiment, and about 3% in a third embodiment. Fructose may be added in addition to or in place of sucrose. Fructose may be added to the soy beverage in amounts from about 0% to about 10% in a first embodiment, from about 1% to about 4% in a second embodiment, or about 2% in a third embodiment. Low calorie or reduced calorie sweeteners may be substituted for sucrose or fructose. Any artificial sweeteners such as aspartame, saccharin and its salts, acesulphame K and glycerrhizinic acid and salts, and their various combinations may also be substituted for or added to the natural sweeteners. The soy beverage can thus be formulated as a product sweetened with natural carbohydrate sweeteners and/or artificial sweeteners.

The flavor of the soy beverage may also be enhanced with flavoring. "Flavoring" refers to any natural or artificial flavoring, or combination thereof. The flavoring may include a variety of flavors including but not limited to strawberry, orange, berry, pineapple, or other fruity flavors. Other flavors such as chocolate, vanilla, etc. may also be used. To further enhance the flavor of the soy beverage, salts, for example, sea salt may be added. Sea salt may be added in amounts to about 0.01% by weight, preferably from about 0.0005% to about 0.005% by weight and more preferably from about 0.001% to about 0.0025% by weight.

"Stabilization aids" refer to any substance that tends to keep the soy beverage solution from changing its physical form, color, or chemical composition. Physical form changes unsatisfactory to the consumer include keeping any pigments and other component including the hydrolyzed soy base, and/or additives in emulsion form and/or in a colloidal suspension. One stabilizing aid is xanthan gum which may be used to keep the water and solids of the soy beverage together in a liquid phase. Xanthan gum may be present in the soy beverage from about 0% to about 0.01% in a first embodiment, from about 0.002% to about 0.008% in a second embodiment, and about 0.005% in a third embodiment. A second stabilization aid used in the soy beverage is lecithin or any derivatives thereof. The lecithin acts as an emulsifier for the oil present in the hydrolyzed soybean base. Lecithin may be present in the soy beverage to about 0.1%, preferably from about 0.005% to about 0.05%, and more preferably about 0.01% to about 0.025%. Guar gum, a second suitable stabilization aid, may be present in a first embodiment to about 0.01%, preferably from about 0.002% to about 0.008%, and more preferably from about 0.004% to about 0.006%. Carboxymethyl cellulose, yet another suitable stabilization aid, may be present in a first embodiment to about 0.01%, preferably from about 0.002% to about 0.008%, and more preferably from about 0.004% to about 0.006%. As will be appreciated by those skilled in the art, other known stabilization aids may be used as desired.

III. Manufacture

There will now be described the inventive process used to manufacture the hydrolyzed soy base and completed soy beverage. FIG. 1 shows a block diagram of the general process of the present invention which includes: providing whole soybeans 100; activating endogenous enzymes of the whole soybeans 110; hydrolyzing proteins of the soybeans 120; hydrolyzing carbohydrates of the soybeans 130; and forming the hydrolyzed soy base 140.

Figure 2:
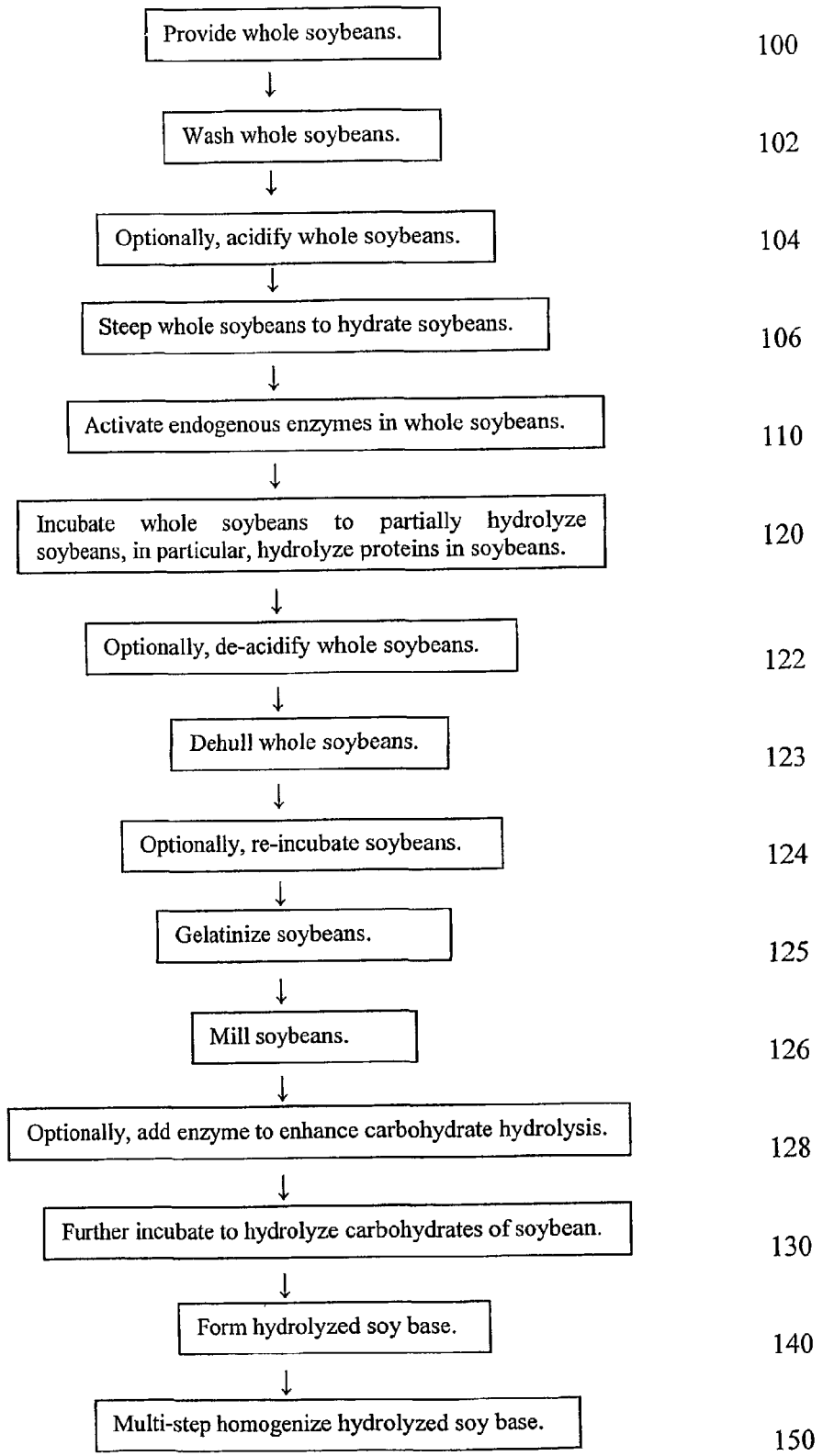
FIG. 2 shows a block diagram of a specific embodiment of a process used to manufacture a soy base.

FIG. 2 shows a block diagram of a process of the present invention corresponding to a particular embodiment, which includes: providing whole soybeans 100; washing the whole soybeans 102; optionally, acidifying the whole soybeans 104; steeping the whole soybeans to hydrate them 106; activating the endogenous enzymes in the whole soybeans 110; incubating the soybeans to partially hydrolyze them, in particular, to hydrolyze proteins in the whole soybeans 120; optionally, de-acidifying the soybeans 122; dehulling the whole soybeans 123; optionally, re-incubating the soybeans 124; gelatinizing the soybeans 125; milling soybeans 126; optionally, adding enzyme to enhance carbohydrates hydrolysis 128; further incubating the milled soybeans to hydrolyze carbohydrates of the soybeans 130; forming a hydrolyzed soy base 140; and multi-step homogenizing the hydrolyzed soy base 150.

The individual steps of the process of the particular embodiment in FIG. 2 are described in full detail below. To begin the process of this embodiment, whole soybeans are mixed and washed with water in a washing vessel.

A. Soybean Hydration

The soybeans may be soaked in water having a temperature from about 15° to about 45° C., preferably about 32° C. and a pH from about 6.0 to about 8.0 preferably at pH of about 6.5 to about 7.5 and more preferably about 7.2. Depending on the temperature of the water, the time the soybeans are soaked may vary. When describing a temperature over a time period herein as "constant," it is meant that the temperature is maintained continuously at about the given temperature. When describing a temperature as an "inlet" temperature, it is meant that the temperature of the liquid or other substance used is initially added with the specified temperature, however, the temperature may change with time due to cooling or warming of the liquid or substance by ambient conditions. When a temperature is used herein without specifying "inlet" or "constant," the temperature may be considered as either an "inlet" or "constant" temperature.

The time necessary for soaking is reduced in warmer soaking water. In one embodiment, soaking the whole soybeans in water, or any other suitable liquid, at about a constant 40° C. for about 8 hours is sufficient In a second embodiment, soaking at about a constant 35° C. for about 12 hours is sufficient. In a third embodiment, soaking at about a constant 20°±2° C. for about 12 hours is sufficient. In another embodiment, soaking at about a constant 15° C. for about 24 hours is sufficient. Accordingly, the soybeans may be soaked in a liquid at a constant temperature of about 40° C. to about 15° C. for about 8 to about 24 hours.

Alternatively, the soybeans may be soaked in an additional embodiment in water having an inlet temperature of about 40° C. for about 12 hours; in another embodiment in water having an inlet temperature of about 35° C. for about 15 hours, and yet another embodiment, in water having an inlet temperature of about 15° C. for about 30 hours. Accordingly, the soybeans may be soaked in water having an inlet temperature of about 40° C. to about 15° C. for about 12 to about 30 hours. As they are soaked, the soybeans are re-hydrated to activate the endogenous enzymes in the soybeans. After sufficient soaking, the water is removed from the mixing vessel and the partially hydrated soybeans are rinsed in water at about 40° C.

Optionally, the soybeans may be soaked, or "steeped," in a liquid having a very low pH. In one embodiment, a food grade acid may be used to lower the pH of a liquid in which soybeans are soaked. For example, a batch of soybeans may be initially added to tap water having a neutral pH of about 6.5 to about 7.5. Concentrated food grade acid may be added to the water to significantly lower the pH. In one embodiment, 50% concentrated food grade citric acid, available from FBC Industries in Rochelle, Ill. is added to an aliquot of water to drop the pH of the water from about 7.2 to about 2.0. Immediately thereafter the soybeans are allowed to soak in the water for periods of time as noted above. In a most preferred embodiment, the soybeans are allowed to soak at 32° C.±2° C. for about 4 hours.

After soaking, the soybeans may be incubated as described below. Optionally, before or after incubation, the soybeans may be de-acidified by soaking the soybeans in tap water or a neutral pH liquid for a selected temperature and time period, for example, water at about 20° C. to about 70° C. for about 60 minutes to about 10 minutes, or more preferably, water at about 55° C. for about 30 minutes.

B. Soybean Incubation

The soybeans are then incubated in a model "L" steam jacketed kettle (BAR, N. A. Inc., Seymour, Ill., United States of America) or other comparable steam kettle or incubator, to further activate the endogenous enzymes. Generally, incubation is the process by which biological matter undergoes physical or chemical changes under certain conditions such as a specific temperature and/or duration. In the process of the present invention, incubation is the process by which soybeans are maintained in a state that is favorable to activate endogenous enzymes in the soybean so that the soybean begins to germinate and partially hydrolyze proteins and/or carbohydrates. In a first process, the soybeans are incubated to about 40° C. for about 10 hours, and may be stirred at least once at the third hour. In another process, the soybeans are incubated at about a constant 35° C. for about 12 hours with the soybeans being stirred, if desired, once at about the 6th hour. In a third process, the soybeans are incubated at about 32°±2° C. for about 18 hours. In a fourth process, the soybeans are incubated at about 25°±2° C. for about 30 hours. In a fifth process, the soybeans are incubated at about 20° C. constant for about 60 hours and may be stirred, if desired, at about the 30th hour. Accordingly, the soybeans may be soaked at a constant temperature of about 40° C. to about 20° C. for about 10 hours to about 60 hours.

After incubation, the soybeans may optionally be re-soaked in water in a kettle to re-soften the soybeans at about a constant 50° C. for about one-half hour in a first embodiment; at about a constant 40° C. for about one and a half hours in a second embodiment; and at about a constant 45° C. for about one hour in a third embodiment. Accordingly, the soybeans may be re-soaked in water having a constant temperature of about 50° C. to about 40° C. for about one-half hour to about one and a half hours. After the re-soaking, the water is removed from the steam jacketed kettle, and the soybeans are rinsed with water to reduce the microbial load of the soybeans. In a first embodiment, this water may be at temperatures from about 15° C. to about 50° C. In a second embodiment, the water may be at about 50° C.

In processes where soybean cultivars are steeped in an acidic solution before incubation, those acidified soybeans may be de-acidified after incubation by soaking the acidified/incubated soybeans in a neutral pH solution, for example, water from a conventional tap.

Optionally, the viability of soybean cultivars may be observed and tested after incubation is complete because incubation partially germinates the soybeans, and germination is an indicator of viability. In one embodiment, after incubation at about 25°±2° C. for about 12 hours, the number of germinated seeds in a selected batch of a particular soybean variety is counted and that count is divided by the total number of seeds in the selected batch and multiplied by 100%. Other attributes of the germinated beans may be measured to further classify seed viability. For example, sprout length, fermentation odor, rancid flavor and grittiness of a soy beverage manufactured according to the process further described in detail below. The results of a particular viability test are explained in further detail in Example 2 below.

C. Dehulling

Next, the soybeans may be dehulled, that is, their skins are removed from the cotyledons of the whole soybeans. Dehulling reduces the fibrous content of the beans, as the hulls are comprised primarily of fiber. A wet-type model BB soybean dehuller (BAR, N. A., Seymour, Ill.) or other comparable dehuller, may be used to dehull the whole soybeans. The dehuller separates the hulls from the cotyledons and the cotyledons are collected. Alternatively, the soybeans may be extracted using conventional physical or chemical processes as will be appreciated by those skilled in the art.

D. Protein Hydrolysis

The cotyledons are further incubated to continue hydrolysis of proteins. A stream jacketed kettle may be used for this purpose. During this step of the process, the soybean proteins are further hydrolyzed. For example, polypeptides, that is, peptide chains having more than ten amino acids, are hydrolyzed to shorter oligopeptides, that is, peptide chains having two to ten amino acids. The cotyledons are incubated at about 45° C. for about 4 to 6 hours, preferably at about 40° C. for about 8 hours, more preferably at about 30° C. for about 10 hours, and most preferably at about 25° C. for about 12 hours. Accordingly, the cotyledons are incubated at about 45° C. to about 25° C. for about 4 hours to about 12 hours. Any temperature and duration of incubation is satisfactory as long as the proteinases in the cotyledons are activated to enzymatically assist in the further hydrolysis of soy proteins in the cotyledons. Additional proteinases or enzymes may be added to the cotyledons to enhance protein hydrolysis.

E. Gelatinization

The protein hydrolyzed cotyledons are then boiled in water for about 25 to about 40 minutes in a first embodiment and about 30 minutes in a second embodiment, in the steam jacketed kettle to induce coagulation and gelatinization of partially hydrolyzed soybeans. "Gelatinization" refers to the formation of a gel or gel-like substance on heating a suspension of polysaccharides or mixtures of polysaccharides and proteins. After boiling, the steam may be turned off. In an alternative embodiment, the cotyledons may be soaked in a solution of food grade buffers, alkali solutions or other solutions as will be appreciated by those skilled in the art, at a temperature of about 65° C. to about 150° C., and a pH of about 6.2 to about 7.5. Examples of suitable food grade buffers are citrate and phosphate; examples of alkali solutions are those including sodium bicarbonate, sodium hydroxide, and/or potassium hydroxide.

F. Milling

The gelatinized cotyledons may be milled with a model 150 BMI stainless steel mill (BAR N. A. Inc., Seymour, Ill.) or other capable mill. "Milling" means physically breaking down the gelatinized cotyledons into a slurry of small particles. In a preferred embodiment, the cotyledons are milled in water at a ratio of about 1 part cotyledon and 8 parts water, or any other ratio as desired.

G. Polysaccharide Hydrolysis

The slurry cotyledon may be incubated to hydrolyze the carbohydrates, that is, the saccharides in the soybeans. For example, cellulose and hemicellulose (known as polysaccharides) are partially hydrolyzed to beta-glucans and sugars. To enhance the breakdown of the carbohydrates, enzyme(s) is/are added to the cotyledon slurry. Cellulase, hemicellulase or a mixture of cellulases is useful, but any other enzyme capable of enhancing the carbohydrate hydrolysis may be used, as will be appreciated by those skilled in the art. In a first embodiment, up to about 10 grams of cellulase per kilogram dry bean weight is added, preferably from about 1 to about 3 grams of cellulase.

Optionally, a cellulase/hemicellulase combination may be used to enhance soybean polysaccharides hydrolysis. Commercially available cellulase/hemicellulase preparation identified by the trademark Laminex bg, available from Genencor of Rochester, New York has been found useful. In one embodiment a 50/50 ratio of 1 ml cellulase: 1 ml hemicellulase enzymes are added to the slurry to facilitate soybean polysaccharide hydrolysis. Usually, addition of cellulase and/or hemicellulase does not significantly increase efficiency of polysaccharide hydrolysis for high viability of soybeans, as the endogenous enzymes of those soybeans sufficiently hydrolyze the polysaccharides. As desired, however, cellulase and/or hemicellulase may be used with high viability soybeans.

The slurry is then mixed in one embodiment at a pH of about 6.0 to 7.0, in another embodiment of about 6.0, followed by incubation of the slurry and cellulase enzymes from about 35° to 55° C. for about 3 hours to about 20 seconds, respectively. After the proteins and carbohydrates of the whole soybeans have been hydrolyzed, the resultant composition is referred to as the "hydrolyzed soybean base."

The cellulase activity in the slurry may be terminated at the end of incubation by heating the slurry in the kettle to about 90° C. for about ½ hour, followed by cooling the slurry to about 60° C. in the kettle.

H. Deodorization

The cooled slurry may be deodorized using conventional vacuum pan or evaporator deodorizing processes which will be appreciated by those skilled in the art. Once the slurry is deodorized and concentrated, it may be cooled to about 20° C. In a first embodiment, the hydrolyzed soy base has a total solids content of about 5% to about 35%, preferably from 10% to about 20%, and more preferably from 13% to about 18%. The total solids content may vary according to the amount of water that bonds to the polysaccharides, or the variety of whole soybeans used in the process.

I. Additional Components

The hydrolyzed soybean base may then be mixed in a mixing tank at about room temperature with sweeteners, flavoring, stabilization aids and coloring as desired in a complete soy beverage. Examples of ingredients that may be added include sucrose, fructose, sea salt, xanthan gum, guar gum, lecithin, flavor, and coloring. After all the ingredients are mixed, the formulation may be stirred and stored at about −20° C. to about 60° C. in a first embodiment, at about 0° to about 10° C. in a second embodiment, and at about 4° C. in a third embodiment.

J. Homogenization

The hydrolyzed soybean base or any resultant formulation may be homogenized. "Homogenization" refers to a mechanical process for creating a colloidal system that is unaffected by gravity. In a first embodiment, the soy base or formulation may be homogenized from about 4,000 psi to about 30,000 psi. In a second embodiment, the soy base or formulation may be homogenized at about 15,000 psi any commercially available homogenizer may be used, for example, a Rannie 12.56 VH Homogenizer (APV Americas, Wilmington, Mass.), or other comparable homogenizer. It will be appreciated by those skilled in the art that the higher the pressure, the more smooth and consistent the formulation will become.

Optionally, the hydrolyzed soy base or formulation may be step-homogenized, that is, it may be homogenized at sequential homogenization pressures. In one embodiment, the hydrolyzed soybean base is homogenized at three successive, increasing pressures, for example, at 2,000 psi, then 3,500 psi and then 14,000 psi. As will be appreciated, the number of sequential homogenization steps, as well as the pressures may be modified as desired.

K. Heat Treatment and Bottling

The homogenized formulation may be sterilized and aseptically packaged. "Sterilization" refers to destruction of bacteria and other infectious organisms in the homogenized formulation or soy beverage. The homogenized formulation may be sterilized in an Armfield FT74DI direct steam injection apparatus, available from Armfield Limited of Hampshire, England, or other comparable sterilizer, at ultra-high temperatures as will be appreciated by those skilled in the art. The formulation is sterilized at temperature of about 150° C. for about 1 to about 2 seconds in a first embodiment, and at about 145° C. for about 5 seconds in a second embodiment. Heat treating at ultra high temperatures for significantly longer periods of time tends to break down the flavoring and coloring of the homogenized formulation. The sterilized homogenized formulation, that is, the resultant soy beverage, may be aseptically packaged to prevent recontamination, in a first embodiment, by hermetic sealing. The sterilized homogenized formulation may be contained in any glass, plastic or other container that is capable of being hermetically sealed. The sterilized homogenized formulation may be stored at room temperature without risk of contamination by bacteria.

The homogenized formulation may alternatively be pasteurized. "Pasteurizing" means killing or inactivating bacterial or other infectious organisms therein. The homogenized formulation may be ultra-pasteurized at about 75° C. to about 99° C. for about one-half hour to about one minute, respectively. The pasteurized homogenized formulation may be stored in any suitable container and then refrigerated.

The resultant soy beverage, that is, either the sterilized, homogenized formulation or the pasteurized, homogenized formulation, may be consumed in the same manner as known for existing beverages.

IV. EXAMPLES

A. Example I

A soy beverage manufactured from hydrolyzed dehulled-whole soybeans according to a process of the present invention was analyzed to determine the nutritional values of the beverage. The sample analyzed was 240 ml and included the ingredients in the amounts noted in Table I, titled "Ingredients of Example I."

TABLE I

Ingredients of Example 1

| Ingredients | Percent Added |
| --- | --- |
| Soymilk base solids | 12 |
| Sucrose | 3 |
| Fructose | 2 |
| Sea salt | 0.001 |
| Xantham gum | 0.005 |
| Guar Gum | 0.005 |
| Lecithin | 0.01 |
| Flavor | 0.5 |
| Color | 0.2 |

Table II below, "Nutritional Facts for Example I," sets forth the measured composition of the hydrolyzed beverage as would be required on "nutrition facts" labels for food by the United States Food & Drug Administration.

TABLE II

Nutritional Facts for Example I

| Nutrient | Amount Per 100 g | Amount Per Serving | % Std. Per Svg |
| --- | --- | --- | --- |
| Basic Components | | | |
| Calories | 53 | 129.85 | |
| Protein | 3.36 g | 8.23 g | 16% |
| Carbohydrates | 5.04 g | 12.35 g | 4% |
| Dietary Fiber | 1 g | 2.45 g | 10% |
| Sugar - Total | 4.58 g | 11.22 g | |
| Fat - Total | 2.19 g | 5.37 g | 8% |
| Saturated Fat | 0.31 g | 0.76 g | 4% |
| Cholesterol | 0 mg | 0 mg | 0% |
| Water | 89.09 g | 218.27 g | |
| Ash | 0.32 g | 0.78 g | |
| Calories from Fat | 19.71 | 48.29 | 8% |
| Vitamins | | | |
| Vitamin A IU | 0 IU | 0 IU | 0% |
| Vitamin C | 0 mg | 0 mg | 0% |
| Minerals | | | |
| Calcium | 17 mg | 41.65 mg | 4% |
| Iron | 0.4 mg | 0.98 mg | 5% |
| Sodium | 80 mg | 196 mg | 8% |

1. Procedure for Manufacture of Example I

Ten kilograms of mixed soybeans were washed twice in 40 liters of water at inlet temperature of 20° C. and rinsed with the same volume of water at 20° C. after each washing. The rinsed soybeans were soaked in 30 liters of water at an inlet temperature of 40° C. at pH 7.0 for 12 hours. The water was drained and the soybeans were rinsed in water at an inlet temperature of 40° C.

The soybeans were placed in a model "L" steam jacketed kettle (BAR, N. A., Inc., Seymour, Ill., United States of America) with the lid closed and incubated at a constant 35° C. for 12 hours, with the soybeans being stirred once at the 6th hour. After incubation, the soybeans were re-soaked in water having an inlet temperature of about 50° C. in the kettle for 30 minutes, drained, and rinsed.

The soaked soybeans were dehulled with a wet-type Model BB soybean dehuller at 20° C. and the wet hulls were separated from the cotyledons by the dehuller.

The soybeans were then hydrolyzed at a constant 40° C. for 8 hours in the kettle with the lid closed.

Once incubated, the cotyledons in the incubation water in the steam jacketed kettle were boiled for 30 minutes to induce gelatinization, after which the steam was turned off. The incubation water was not drained.

The boiled cotyledons were milled into a slurry with a model 150 BMI stainless steel mill using the incubation water as mill water. Cellulase, in particular, Multifect cl (Genencor, Rochester, N.Y.) was added to the slurry in the kettle in the amount of 1 to 3 grams per kg dry bean weight at a pH of 6.0. Thereafter, the slurry with cellulase was incubated at a constant 50° C. for 1 hour. The cellulase activity in the slurry was terminated by heating the slurry in the kettle to 90° C. for 30 minutes, followed by cooling to 60° C. in the kettle by passing 17° C. inlet temperature water through jacket.

The cooled slurry was transferred to a vacuum pan and evaporated until slurry solids was 15%. The deodorized slurry was pumped into the kettle and cooled with water at 20° C. inlet temperature to form the hydrolyzed soybean base.

The hydrolyzed soybean base was mixed in a mixing tank at 20° C. with the ingredients of Table I above to create a beverage formulation. Once mixed, the formulation was stirred and stored at 4° C. Next, the formulation was homogenized at 15,000 psi in a Rannie 12.56 VH Homogenizer.

A first aliquot of the homogenized formulation was sterilized at 150° C. for 2 seconds in an Armfield FT74DI direct steam injector to produce a sterile soy beverage. The sterile soy beverage was aseptically filled in 330 ml plain glass bottles with rubber-lined caps to hermetically seal the bottles. A second aliquot of the homogenized formulation was pasteurized at 80° C. for 30 minutes and filled into sterile 330 ml plain glass bottles.

The sterilized samples were stored at room temperature of 20° to 22° C., and the pasteurized samples were stored at a refrigerated temperature of about 2° to about 4° C. All samples were observed for signs of instability, specifically coagulation, colloidal separation, sedimentation, or formation of fat and/or whey layering.

2. Storage Stability

The samples of enzyme-treated, dehulled-whole soy beverage that were homogenized at 15,000 psi and sterilized were stored at about 20° C. and observed for occurrence of coagulation, residue, and formation of whey for 17 months. The pasteurized samples were stored at about 3°±1° C. and observed for three months. No separation of fat, sedimentation, or coagulation occurred in the sterilized samples or the pasteurized samples.

3. Consumer Acceptance Tests

An informal population of consumers of about 40 people from ages 18 to 65 were asked to rate the color, aroma, taste, mouthfeel (chalkiness), aftertaste, and detection of soy flavor. The consumers were asked to evaluate the product as highly accepted, accepted, or rejected.

The results of a preliminary consumer test of the stabilized soy beverages are below in Table III, titled "Preliminary Consumer Acceptance."

TABLE III

Preliminary Consumer Acceptance

| Sensory Attribute | Accepted/Rejected |
| --- | --- |
| Color | Highly accepted |
| Aroma | Highly accepted |
| Taste | Highly accepted |
| Mouthfeel (chalkiness) | Extracted variety (highly accepted) |
| | Dehulled-whole variety homogenized at 4,500 psi (marginally accepted) |
| | Dehulled-whole variety homogenized at 15,000 psi (highly accepted) |
| Aftertaste | No aftertaste (Accepted) |
| Soy flavor | Completely absent (Accepted) |

Additionally, no discernable changes in the sensory attributes of the sterilized sample stored for 17 months occurred when informally tested by consumers.

Based on the above preliminary consumer study, the soy beverage made according to the process of the present invention has sensory attributes that are highly acceptable to consumers. The product also exhibits excellent stabilization to resist aesthetically displeasing coagulation, sedimentation or coagulation that previously required soy beverages to be stored and marketed in opaque containers.

B. Example 2

A soy beverage was manufactured from hydrolyzed dehulled-whole soybeans of different varieties according to the process of the present invention. The soy beverage was analyzed to determine the effect of soybean viability on soy beverage quality. Six specific food/beverage grades cultivars of varying viability were selected for the analysis, including soybean cultivars that are identified by the names Iowa 3006, Callahan 5200, Iowa 2025, Vinton 81, Ohio-Vinton 81 and Wisconsin 2750, available from Thumb Oilseeds Producers Cooperative, Ubly, Mich., United States of America. As will be appreciated, the viability of other soybean cultivar samples may be tested and used to manufacture the hydrolyzed soybean base of the present invention as desired.

In the viability test, the viability of each variety was calculated. To do this, each of six batches of different varieties was soaked for 12 hours in tap water of pH of about 7.2 and at about 20°±2° C. to hydrate the soybeans. Following hydration, each batch was incubated at about 25°±2° C. for 30 hours. Thereafter, the viability of each of six soybean cultivars was evaluated by counting seeds with visible signs of germination in two drawn samples of approximately 150 seeds per sample.

Seed viability of each of the cultivars was numerically classified by calculating a percent germination, that is, the number of germinated seeds were divided by the total number of seeds in the sample and multiplied by 100%. Additionally, sprout length was evaluated by measuring the length of each sprout in the drawn sample in millimeters (mm) and the mean was calculated. Fermentation odor was evaluated in the soybean immediately after incubation by sniffing.

After viability testing, each of the six batches of different cultivars were manufactured into a hydrolyzed soybean base according to the process of the present invention. Next, two quality indices of the hydrolyzed soybean base—(a) the presence of rancid flavor development and (b) grittiness in the upper palate of the mouth, also referred to as mouth feel—were evaluated by two expert judges that have sensorily evaluated soy milk for 10 years and 12 years respectively. All samples were chilled at 4°±2° C. before sensory evaluation. Notably, the hydrolyzed soybean base contained no flavor additives that would effect the rancid flavor testing.

The results of viability testing are below in Table IV, titled "Effect of Soybean Seed Cultivar/Viability on Soy Base Quality."

TABLE IV

Effect of Soybean Seed Cultivar/Viability on Soy Base Quality

| | \multicolumn{6}{c}{Soybean seed cultivar} | | | | | |
|---|---|---|---|---|---|---|
| | Iowa 3006 | Callahan 5200 | Iowa 2025 | Vinton 81 | Ohio-Vinton 81 | Wisconsin 2750 |
| % Germination (viability) | 16.4 | 9.1 | 11.1 | 93.4 | 82.4 | 93.2 |
| Mean sprout length (mm) | 4.9 | 4.1 | 5.7 | 14.8 | 11.5 | 12.9 |
| Fermentation odor | mild | strong | strong | none | none | none |
| Soymilk rancid flavor | strong | strong | mild | absent | absent | absent |
| Grittiness (mouth feel) | strong | strong | strong | absent | absent | absent |

Based on the above evaluation it was determined that hydrolyzed soy base quality decreases with decrease in soybean seed viability, that is, percent germination of the soybeans. Rancid flavor was dominant in the soy base produced from beans with very low viability, for example, less than 30% germination. These samples also had objectionable mouth feel. Low viability seeds partially or wholly lost endogenous enzyme activity and therefore were inhibited in germination. Re-hydration or incubation of such seeds did not induce germination. It was therefore surmised that hydrolysis of macromolecules by endogenous enzymes of seeds that occurs during germination was therefore inhibited. A further possible explanation is that contaminating microorganisms induced fermentation of the soybeans in place of germination. Accordingly, deterioritive changes occurred that caused objectionable sensory properties as indicated in Table IV. Thus, it is desirable to utilize intermediate to high viability soybeans to manufacture hydrolyzed soybean base. Of course, low viability beans may be used for an application that does not depend on sensory properties, for example, in animal feed.

C. Example 3

A soy beverage manufactured from hydrolyzed dehulled-whole soybeans according to process of present invention was tested to determine the effect of acid steeping of soybeans on processed soy beverage quality.

In the test, three kilograms each of two food/beverage soybean cultivars, EC 1 and HP 204, available from Soyatech, Inc., Bar Harbor, Me., United States of America were washed and put into tap water. The pH of the water was adjusted from 7.2 to 2.0 with 50% concentrated food-grade citric acid available from FBC Industries of Rochelle, Ill. Immediately thereafter, the beans were steeped at 32°±2° C. for about four hours. Steeping was repeated for the two soybean cultivars at pH 3.0, pH 4.0 and pH 5.0 for the same time and temperature as above, but the concentration of citric acid added was manipulated.

After steeping was complete, the steep liquor was drained and the soybeans were incubated at about 32°±20° C. for 18 hours. After incubation, seed viability, that is, percent germination, sprout length and fermentation odor were evaluated as described in Example 2.

The acidified and incubated soybeans were de-acidified and re-soaked by steeping the soybeans in tap water at 55° C. for about 30 minutes. A hydrolyzed soybean based was then manufactured with each incubated soybean cultivar as described above, except that a three-step homogenization process was used on the milled soybeans. Specifically, the milled soybeans were homogenized at 2,000 psi, 3,500 psi and 14,000 psi.

Thereafter, the organoleptic qualities of the soybeans, including color, odor, taste, rancid flavor, and grittiness of the resultant hydrolyzed soybean base were evaluated in samples chilled at 4°±2° C. Two experienced soymilk judges who have sensorily evaluated soymilk for 10 and 12 years, respectively, performed the evaluation. In the evaluation, a four point scale was used, wherein 0 indicates highly acceptable, 0.5 indicates acceptable, 1 indicates indifferent, and 2 indicates rejection. The results of this sensory evaluation are set forth below in Table V, titled "Effect of Citric Acid Steeping on Soybean Germination and Sensory Quality of Unsweetened and Unflavored Soy Base Produced from Two Soybean Cultivars."

TABLE V

Effect of Citric Acid Steeping on Soybean Germination and Sensory Quality of Unsweetened and Unflavored Soy Base Produced from Two Soybean Cultivars

| | \multicolumn{8}{c}{pH} | | | | | | | |
|---|---|---|---|---|---|---|---|---|
| | 2.0 | | 3.0 | | 4.0 | | 5.0 | |
| | \multicolumn{8}{c}{Soybean cultivar} | | | | | | | |
| Quality attribute | EC 1 | HP 204 | EC 1 | HP 204 | EC 1 | HP 204 | EC 1 | HP204 |
| % Germination | 20 | 13.5 | 69 | 75 | 69.7 | 71.2 | 80.4 | 72.3 |

TABLE V-continued

Effect of Citric Acid Steeping on Soybean Germination
and Sensory Quality of Unsweetened and Unflavored Soy Base Produced
from Two Soybean Cultivars

| | pH | | | | | | | |
|---|---|---|---|---|---|---|---|---|
| | 2.0 | | 3.0 | | 4.0 | | 5.0 | |
| | Soybean cultivar | | | | | | | |
| Quality attribute | EC 1 | HP 204 | EC 1 | HP 204 | EC 1 | HP 204 | EC 1 | HP204 |
| Sprout length (mm) | 3.0 | 1.7 | 8.2 | 5.5 | 10 | 6.8 | 17 | 6.8 |
| Fermentation odor | absent | absent | absent | absent | absent | absent | absent | absent |
| Soy base color (whiteness) | 1, 0.5 | 0, 1 | 0, 0.5 | 1.5, 1 | 0, 0 | 1.5, 2 | 0, 0. | 2, 2 |
| Soy base odor | 0.5, 0 | 0.5, 0 | 0, 0 | 0.5, 0.5 | 0, 0 | 0, 1 | 0, 0 | 0, 0 |
| Soy base taste | 0, 0 | 1, 0 | 0, 0 | 1, 0.5 | 0, 0 | 0, 0 | 0, 0 | 0.5, 0 |
| Rancid flavor | 0, 0 | 0, 0 | 0, 0.5 | 0.5, 0.5 | 0, 0. | 0, 0 | 0, 0 | 0, 0 |
| Mouth feel (grittiness) | 0, 0 | 0, 0 | 0, 0 | 0, 0 | 0, 0 | 0, 0 | 0, 0 | 0, 0 |

As evident from Table V above, the sensory characteristics of the hydrolyzed soybean base were affected differently by citric acid steeping of soybeans. Although grittiness of the hydrolyzed soybean base was eliminated at all the pH levels studied, rancid flavor was marginally detected at some levels including pH 3 and pH 4. Conversely, soy base color showed the greatest variation with pH. Darker hues were detected at higher pHs in the hydrolyzed soybean base made with HP 204 soybean cultivar compared to EC 1 cultivar. Soybean odor and taste were marginally detected at a lower pH.

Notably, germination rates generally increased at higher pH levels and the typical fermentation odor was completely undetected, indicating inhibition of contaminating microorganisms. Overall, citric acid steeping of high viability soybeans coupled with three-step homogenization of the slurry of high viability soybeans improved the sensory characteristics of the hydrolyzed soybean base.

D. Example 4

A hydrolyzed soybean base manufactured from hydrolyzed dehulled-whole soybeans according to the process of the present invention was analyzed to determine the effect of high viability soybeans on sensory properties of sweetened/flavored soy beverages.

In the analysis, three kilograms of a food/beverage grade soybean cultivar of Vinton 81 variety exhibiting 93% germination was used to produce a sweetened-flavored soy beverage. The hydrolyzed soybean base was produced as described in the preferred embodiment, except that a cellulase/hemicellulase enzyme combination was added in a ratio of 1 milliliter:1 milliliter of the concentrated enzymes per kilogram of dry soybean weight. The hydrolyzed soybean base with added enzymes then was incubated as described in the preferred embodiments. The resultant flavored soy-based beverage was formulated into a mix in a mixing tank at room temperature at about 20°±2° C. with the ingredients below in Table VI, titled "Ingredients for Example IV."

TABLE VI

Ingredients for Example IV

| Ingredients | Percent Added |
|---|---|
| Soybean base solids | 7 |
| Sucrose | 5 |
| Corn Syrup | 0.5 |
| Sea salt | 0.001 |
| Peach flavor (natural/artificial) | 3 ml per liter of mix |
| Apricot (natural) | 2 ml per liter of mix |
| Color | 2 ml per liter of mix |

No beverage stabilizer or emulsifier was added to the base or mix, as the mix good stability and no formation of colloids. The peach and apricot flavors are available from Carmi Flavors, Inc., Commerce, Calif., United States of America. The formulated mix was homogenized at 4,500 psi, pasteurized and chilled as described above to the preferred embodiment.

For the evaluation, a five-point sensory evaluation scale was used by 10 trained judges to evaluate chilled, flavored, sweetened soy beverages for color, aroma, taste and mouth feel. In the evaluation, 1 indicates dislike very much, 2 indicates dislike, 3 indicates neither like nor dislike, 4 indicates like and 5 indicates like very much. More general scores of 1 and 2 indicated rejection and scores of 3, 4 or 5 indicated acceptance. The results of the evaluation of the chilled flavored, sweetened and colored soy beverage are below in Table VII, titled "Sensory Evaluation of Flavored, Sweetened and Colored Soy Beverage Produced From Vinton 81 Cultivar."

TABLE VII

Sensory Evaluation of Flavored, Sweetened and
Colored Soy Beverage Produced From Vinton 81 Cultivar

| | Sensory Attribute | | | |
|---|---|---|---|---|
| Judge | Color | Aroma | Taste | Mouth feel |
| 1 | 5 | 5 | 5 | 5 |
| 2 | 5 | 4 | 5 | 5 |
| 3 | 5 | 5 | 5 | 5 |

TABLE VII-continued

Sensory Evaluation of Flavored, Sweetened and
Colored Soy Beverage Produced From Vinton 81 Cultivar

| | Sensory Attribute | | | |
|---|---|---|---|---|
| Judge | Color | Aroma | Taste | Mouth feel |
| 4 | 5 | 5 | 5 | 5 |
| 5 | 3 | 4 | 4 | 4 |
| 6 | 5 | 5 | 5 | 5 |
| 7 | 5 | 4 | 5 | 4 |
| 8 | 5 | 4 | 5 | 4 |
| 9 | 5 | 5 | 5 | 5 |
| 10 | 5 | 5 | 5 | 5 |
| Total | 48 | 46 | 49 | 47 |
| Average | 4.8 | 4.6 | 4.9 | 4.7 |

As evident from Table VII above, use of a high-viability soybean cultivar in sweetened and flavored soy beverages enhanced the beverage acceptability. The 10 trained judges indicated acceptance of the soy beverage with an overall mean score of 95%. The sensory attribute that produced the highest mean score of 4.9/5.0 was taste. Thus, the taste of the flavored soy beverage was highly acceptable to all judges in the evaluation. As also evident, the high-viability soybeans partly caused the decrease in grittiness in the soy beverage.

Notably, mouth feel of soy beverage was highly acceptable, even in the absence of added beverage stabilizers and emulsifiers. In addition, no separation of the fat phase of the beverage was observed, and no sedimentation occurred which indicated adequate emulsification stabilization. This strongly suggests that the polysaccharides in the soybeans, in particular, the soy fiber, was substantially solubilized to produce a partially soluble complex carbohydrate which mimics the effect of a stabilizer. Accordingly, the soy beverage manufactured according to the process of the present invention in the present study appears suitable for manufacturing widely acceptable flavored whole soy beverages.

E. Example 5

A hydrolyzed soybean base manufactured from hydrolyzed dehulled-whole soybeans of high viability according to the process of the present invention was analyzed to determine the nutritional values of the beverage.

Specifically, a chemical analysis of three food/beverage grade soybean cultivars manufactured, was performed by a consulting laboratory, Warren Analytical Laboratory of Greeley, Colo. The analyzed hydrolyzed soybean base was manufactured by first steeping 3 kilograms each of soybean cultivars, including Vinton 81, Ohio-Vinton 81 and Wisconsin 2750, available from Thumb Oilseeds Producers Cooperative, Ubly, Mich., United States of America in a citric acid solution at pH 4 at 32°±2° C. for about 4 hours. The citric acid solution was drained and each of the soybean cultivars were incubated at 32°±2° C. for 18 hours in tap water. The soybeans were then de-acidified by steeping the soybean cultivars in tap water at 55° C. for 30 minutes. The hydrolyzed soybean base was then manufactured as explained above with reference to the preferred embodiment. This hydrolyzed soybean base was homogenized using three-step homogenization at 2,000 psi, 3,500 psi and 14,000 psi. The results of the chemical analysis are set forth below in Table VIII, titled "Compositional Analysis of Soy Base Produced in High Viability Food/Beverage Grade Soybean Cultivars Treated with Citric Acid."

TABLE VIII

Compositional Analysis of Soy Base Produced in High Viability
Food/Beverage Grade Soybean Cultivars Treated with Citric Acid

| | Soybean Cultivar | | | | | |
|---|---|---|---|---|---|---|
| | Wisconsin 2750 | | Ohio-Vinton 81 | | Vinton 81 | |
| Component | Amount per 100 g | Amount per 245 g serv. | Amount per 100 g | Amount per 245 g serv. | Amount per 100 g | Amount per 245 g serv. |
| Water | 93.2 g | 228.1 g | 93.2 g | 228.2 g | 92.5 g | 226.5 g |
| Ash | 0.3 g | 0.8 g | 0.4 g | 0.9 g | 0.4 g | 1.0 g |
| Fat - total | 0.3 g | 0.8 g | 0.9 g | 2.3 g | 0.7 g | 1.8 g |
| Saturated fat | 0.0 g | 0.1 g | 0.1 g | 0.2 g | 0.1 g | 0.2 g |
| Protein | 2.8 g | 6.9 g | 3.2 g | 8.0 g | 3.4 g | 8.4 g |
| Carbohydrates | 3.4 g | 8.3 g | 2.3 g | 5.5 g | 3.0 g | 7.3 g |
| Dietary fiber | 1.2 g | 2.9 g | 0.8 g | 1.9 g | 1.2 g | 2.9 g |
| Sugar - total | 0 g | 0 g | 0 g | 0 g | 0 g | 0 g |
| Cholesterol | 0 mg | 0 mg | 0 mg | 0 mg | 0 mg | 0 mg |
| Calories - total | 28 | 68.5 | 30 | 73.4 | 32 | 78.3 |
| Calories from fat | 3.0 | 7.3 | 8.5 | 20.7 | 6.5 | 15.9 |

The chemical analysis of Table VIII shows that the hydrolyzed soybean base produced from the three high viability soybean cultivars includes many beneficial attributes. Included in the attributes are low saturated fat content of 0% to 0.1%, total sugar of 0% and high dietary fiber values of 0.8% to 1.2%. Protein values range from 6.9 grams to 8.4 grams per serving, which are greater than the 6.25 grams per 245 grams (8 oz.) beverage serving size recommended by the United States Food and Drug Administration. The total solids content of the hydrolyzed soybean bases range from 6.8% to 7.5%. The low saturated fat content of the hydrolyzed soybean base makes that base suitable for people prone to cardiovascular diseases.

F. Example 6

A hydrolyzed soybean base manufactured from hydrolyzed dehulled-whole soybeans according to a process of the present invention utilizing a special carbohydrate enzyme was analyzed. The fatty acid profile of this fully hydrolyzed soybean base was compared with (1) an unhydrolyzed soybean base and (2) a partially hydrolyzed soybean base to demonstrate the enhanced nutritional value of fully hydrolyzed soybean bases.

One food/beverage grade intermediate viability soybean cultivar, Callahan 5200, was used to prepare samples. Three samples were prepared corresponding to (a) an unhydrolyzed (control) sample, (b) a partially hydrolyzed sample, and (c) a fully hydrolyzed soybean sample. For the unhydrolyzed sample, three kilograms of soybeans were steeped to tap water at 20°±2° C. for 12 hours, drained, rinsed and dehulled. The cotyledons were then boiled and gelatinized and milled to create an unhydrolyzed soybean base. No enzyme was added.

For the partially hydrolyzed sample, three kilograms of soybeans were steeped in tap water at 20°±2° C. for about 12 hours. The sample was then drained, rinsed and incubated at about 25°±20° C. for 30 hours. The incubated soybeans were then re-soaked, dehulled and further incubated at 55° C. for 3 hours. The cotyledons were gelatinized by boiling and then milled to create a partially hydrolyzed soybean base. No enzyme was added.

For the fully hydrolyzed sample, three kilograms of whole soybeans were steeped in tap water at about 20°±2° C. for 12 hours, drained, rinsed and dehulled. Three kilograms of soybeans were steeped in tap water at 20°±2° C. for about 12 hours. The sample was then drained, rinsed and incubated at about 25°±2° C. for 30 hours. The incubated soybeans were then re-soaked, dehulled and further incubated at 55° C. for 3 hours. The cotyledons were then gelatinized by boiling and then milled to create a partially hydrolyzed soybean base. 1.2 milliliters of a cellulase preparation, Multifect cl, and 0.8 milliliters of another cellulase/hemicellulase preparation, Laminex bg, both available from Genencor of Rochester, N.Y., were added to 2 liters of the hydrolyzed soybean base. The 2 liter sample was then properly mixed and dispensed into 1 liter capacity beakers, covered with aluminum foil and incubated at 55° C. for 2 hours. Larger sample sizes were combined and prepared and homogenized at 4,500 psi followed by pasteurization at 75° C. for 40 minutes. Thereafter, the samples were chilled and sent in cold packs to a consulting laboratory, Silliker Labs of Chicago Heights, Ill., to perform a fatty acid and fiber analysis of the resultant un-hydrolyzed soybean base, the partially hydrolyzed soybean and fully hydrolyzed soybean base prepared as explained above. The results of this analysis is below in Table IX, titled "Fatty Acid Profile and Dietary Fiber of Soy Bases."

TABLE IX

Fatty Acid Profile and Dietary Fiber of Soy Bases

| Quality Attribute | Unhydrolyzed (control) | Partially hydrolyzed | Fully hydrolyzed |
|---|---|---|---|
| Total saturated fatty acid | 27.8 | 27.2 | 19.8 |
| Total mono-unsaturated | 30.0 | 25.7 | 27.7 |
| Total poly-unsaturated | 42.0 | 47.1 | 52.2 |
| Insoluble dietary fiber (g) | 0.46 | 0.11 | 0.27 |
| Soluble dietary fiber (g) | 0.29 | 0.57 | 0.41 |

As evident from Table IX, total saturated fatty acids concentration decreased 8% in the fully hydrolyzed, dehulled-whole soy base relative to the un-hydrolyzed (control) sample. Conversely, a 10.2% increase in total poly-unsaturated fatty acids occurred in the fully hydrolyzed sample compared to the control. Minor changes in concentration of mono-unsaturated fatty acid content occurred. A 41% increase in soluble dietary fiber content was observed in a partially hydrolyzed sample relative to the control. Notably, the soluble dietary fiber produced by enzyme hydrolysis of insoluble soy fiber in the present study minimizes or possibly eliminates the need to add to the soy beverage a stabilizer, that is, a polysaccharide that binds water in food/beverage systems to prevent sedimentation of colloids.

G. Example 7

To evaluate the isoflavone variability in soy bases given different hydrolytic treatments the following samples of soybeans were analyzed and compared to one another: (1) a fully incubated and hydrolyzed with cellulase sample; (2) a partially incubated/fermented sample; and (3) a control sample which was not incubated or acted upon by enzymes. For the control sample, three kilograms of intermediate viability food/beverage grade soybeans of the variety Iowa 2032 were washed, steeped in tap water at 20° C.±2° C. for 12 hours, drained, rinsed, dehulled and milled. Three kilograms dry weight whole soybeans produced 33 liters of slurry which was homogenized at 4,500 psi. For the partially incubated/fermented sample, three kilograms of Iowa 2032 soybeans were steeped at 45° C. and then left at 20°±2° C. for 6 hours, drained and rinsed. The soybeans were then incubated at 25°±2° C. for 48 hours. At 48 hours, fermentation was detected via odor, stickiness of seeds, and low percent germination (less than 25%). The incubated seeds were re-soaked, dehulled, gelatinized by boiling and milled. Three kilograms dry weight of soybeans produced 33 liters of slurry which was homogenized to 4,500 psi and pasteurized at 75° C. for 40 minutes.

For the sample that was fully incubated and hydrolyzed with cellulase, three kilograms of Iowa 2032 soybeans were steeped at 20°±2° C. for 12 hours, drained and rinsed. The soybeans were then incubated at 25°±2° C. for 30 hours, re-soaked at 45° C. for 30 minutes and dehulled. The cotyledons were then incubated at 55° C. for 3 hours, gelatinized by boiling and milled. Three kilograms dry weight whole soybeans produced 33 liters of slurry. To this slurry, a cellulase/hemicellulase enzyme combination of Laminex bg and Multifect cl was added so that the concentrations of the enzymes in the slurry were the same as in the Example 6. The slurry and enzymes were mixed and re-incubated at 55° for 3 hours. Thereafter, the slurry and enzyme mixture was homogenized at 4,500 psi and pasteurized at 75° C. for 40 minutes.

For the fully incubated without cellulase sample, three kilograms of Iowa 2032 soybeans were processed as above as described in connection with a fully incubated hydrolyzed with cellulase sample, except that the cellulase/hemicellulase enzymes were not added.

To determine isoflavone variability among the three test samples, the concentrations of select isoflavone forms were analyzed. A first set of isoflavones analyzed included genistein and daidzein, which are "active" forms of isoflavones that are absorbed in the gut. A second set of isoflavones analyzed included genistin and daidzin, which are storage forms of isoflavones. The concentrations of the various isoflavones (in micrograms per gram sample) in the various samples are indicated in Table X, titled "Isoflavone Variability in Soy Bases" set forth below.

TABLE X

Isoflavone Variability in Soy Bases

| | Isoflavone Type | | | | | |
|---|---|---|---|---|---|---|
| Soybean Treatment | Daidzin | Ginistin | Daidzein | Geinistein | Sums of individual Daidzein isomers | Sums of individual Geinistein isomers |
| No incubat. | 624 | 645 | 17 | 18 | 653 | 663 |
| (control) | 653 | 676 | 17 | 18 | 673 | 695 |
| Partial incub. + | 595 | 681 | 48 | 44 | 657 | 721 |
| fermen. | 612 | 686 | 50 | 45 | 675 | 736 |
| Full incubat. + | 338 | 422 | 207 | 216 | 624 | 699 |
| cellulase | 356 | 444 | 216 | 224 | 654 | 730 |
| Full incubat. | 598 | 676 | 32 | 23 | 649 | 705 |
| no cellulase | 591 | 678 | 33 | 25 | 670 | 728 |

As evident from Table X, the concentration of genistein and daidzein in the filly incubated sample increased by greater than 1,000% when compared to the non-incubated (control) sample.

In the digestive system, the storage forms of soybean isoflavones genistin and daidzin are converted by intestinal fermentation plus the action of digestive juices to the absorbed forms, that is, the aglycones, genistein and daidzein. From Tables IX and X, it is evident that cellulase addition and incubation in the present study produced the combined effect of hydrolyzing soybean complex carbohydrates (Table IX) and the conversion of storage isoflavones to the active forms (Table X). The data in Table X shows that the samples to which the cellulase was not added shows much lower conversion. Thus, soy beverages manufactured by the process described in the present invention appear to have enhanced biological value by way of the potentiated soybean isoflavones.

The above descriptions are those of preferred embodiments of the invention. Various alterations and changes can be made without departing from the spirit and broader aspects of the invention as defined in the claims, which are to be interpreted in accordance with the principles of patent law, including the doctrine of equivalents. As used in the specification, the term "includes" or "including" is understood to mean "includes but is not limited to." Except in the claims and the specific examples, or where otherwise expressly indicated, all numerical quantities in this description indicating amounts of material, reaction conditions, use conditions, molecular weights, and/or number of carbon atoms, and the like, are to be understood as modified by the word "about" in describing the broadest scope of the invention. Any reference to an item in the disclosure or to an element in the claim in the singular using the articles "a," "an," "the," or "said" is not to be construed as limiting the item or element to the singular unless expressly so stated. Unless otherwise expressly indicated, all percentages in the claims are weight percentages based on the total weight of the composition. Further, measurements of enzymes in grams are in grams per kilogram dry soybean weight unless otherwise indicated.

The embodiments of the invention in which an exclusive property or privilege is claimed are defined as follows:

1. A process for manufacturing a soybean base product from whole soybean cotyledons comprising:

providing whole soybean cotyledons including endogenous enzymes, proteins, and carbohydrates;

incubating the whole soybean cotyledons at a first temperature and for a first duration sufficient for the endogenous enzymes to at least partially hydrolyze the proteins but insufficient for the endogenous enzymes to hydrolyze the carbohydrates; and incubating the whole soybean cotyledons in another, subsequent step at a second temperature and for a second duration sufficient for the endogenous enzymes to hydrolyze the carbohydrates to form a soybean base product, the soybean base product being substantially incapable of cross-linking to form colloidal conjugates.

2. The process of claim 1 further comprising using an additional enzyme to enhance hydrolyzing at least one from the proteins and the carbohydrates.

3. The process of claim 2 further comprising milling the whole soybean cotyledons.

4. The process of claim 2 further comprising hydrating the soybean cotyledons to initiate activation of the enzymes.

5. The process of claim 4 wherein the cotyledons are soaked in a liquid at a constant temperature of about 40° C. to about 15° C. for about 8 to about 24 hours during said hydrating.

6. The process of claim 4 wherein the soybean cotyledons are soaked in a liquid having an inlet temperature of about 40° C. to about 15° C. for about 12 to about 30 hours during said hydrating.

7. The process of claim 4 wherein the soybean cotyledons are soaked in a liquid having a pH of about 2 to about 4.

8. The process of claim 4 wherein the soybeans are hydrated in a liquid including a food/beverage grade acid.

9. The process of claim 2 further comprising dehulling the whole soybean cotyledons.

10. The process of claim 2 wherein the whole soybean cotyledons are incubated during said incubating at a constant temperature of about 40° C. to about 20° C. for about 10 hours to about 60 hours.

11. The process of claim 10 further comprising soaking the whole soybean cotyledons in a liquid having a constant temperature of about 50° C. to about 40° C. for about 1 hour to about 1.5 hours after said whole soybean cotyledon incubating.

12. The process of claim 1 wherein the whole soybean cotyledons are of a variety that exhibit greater than 70% germination when incubated.

13. A method for producing a soybean base comprising:
providing whole soybeans that include proteins, carbohydrates, and endogenous enzymes;
steeping the soybeans in water to activate the endogenous enzymes;
draining the water from the soybeans;
incubating the soybeans to hydrolyze the proteins at a first temperature sufficient to prevent cross-linking of the proteins with the carbohydrates and to prevent formation of visible colloidal conjugates; and
reincubating the soybeans at a second temperature greater than the first temperature to hydrolyze the carbohydrates of the slurry with the endogenous enzymes to form a soybean food base, wherein the reincubating carbohydrate hydrolyzing step is carried out after the incubating, protein hydrolyzing step.

14. The method of claim 13 wherein the endogenous enzymes include proteinases and cellulases naturally present in the whole soybeans.

15. The method of claim 14 wherein said protein hydrolyzing includes incubating the cotyledons at a temperature and a duration of time sufficient to cause the proteinases to hydrolyze the proteins in the cotyledons.

16. The method of claim 15 wherein said cotyledons are incubated during said protein hydrolyzing at a temperature of about 45° C. to about 25° C. for about 6 hours to about 12 hours.

17. The method of claim 16 further comprising adding to the slurry an enzyme capable of enhancing carbohydrate hydrolysis.

18. The method of claim 17 further comprising incubating the slurry at a temperature and a duration of time sufficient to activate the added enzyme so that the added cellulase at least partially hydrolyze the carbohydrates in the slurry.

19. The process of claim 17 further comprising adding to the soybean food base ingredients chosen from sweeteners, flavoring, stabilization aids, and coloring.

20. A soybean food base produced by the process of claim 13 wherein the hydrolyzed soybean food base is without visible colloid conjugates.

21. A soybean food base produced by the process of claim 19 wherein the hydrolyzed soybean food base is without visible colloid conjugates.

22. A soybean food base produced by the process of claim 14 wherein the hydrolyzed soybean food base is without visible colloid conjugates.

23. A soybean food base produced by the process of claim 17 wherein the hydrolyzed soybean food base is without visible colloid conjugates.

24. A process for manufacturing a soybean product comprising:
providing whole soybeans;
hydrolyzing proteins present in the whole soybeans at a first temperature and for a first duration insufficient to substantially hydrolyze carbohydrates present in the whole soybeans; and
hydrolyzing carbohydrates present in the whole soybeans at a second temperature and for a second duration sufficient to substantially hydrolyze the carbohydrates present in the whole soybeans whereby the hydrolyzed proteins and hydrolyzed carbohydrates are incapable of cross-linking to form colloidal conjugates.

25. The process of claim 24 comprising adding enzymes to increase the rate at which carbohydrates are hydrolyzed during said hydrolyzing carbohydrates.

26. The process of claim 25 wherein the enzyme is at least one of a cellulase and a hemicellulase.

27. The process of claim 24 comprising selecting high viability whole soybeans.

28. The process of claim 24 wherein comprising gelatinizing the whole soybeans.

29. The process of claim 28 comprising homogenizing the gelatinized soybeans at a plurality of different pressures.

30. The process of claim 24 wherein the whole soybeans are soaked in a liquid at a pH of about 6 to about 8.

31. The process of claim 30 wherein the soybeans are soaked in a liquid at a pH of about 2 to about 4.

32. The process of claim 30 comprising adding a food grade acid to the liquid to reduce the pH of the liquid.

* * * * *